United States Patent [19]

Durden, Jr.

[11] 4,304,735

[45] Dec. 8, 1981

[54] N-[4-(TERT-BUTYL)PHENYLSULFENYL]-N-ALKYLCARBAMOYL FLUORIDE COMPOUNDS

[75] Inventor: John A. Durden, Jr., South Charleston, W. Va.

[73] Assignee: Union Carbide Corporation, New York, N.Y.

[21] Appl. No.: 81,376

[22] Filed: Oct. 3, 1979

Related U.S. Application Data

[63] Continuation of Ser. No. 710,738, Aug. 2, 1976, abandoned.

[51] Int. Cl.³ .......................................... C07C 125/03
[52] U.S. Cl. ................................................ 260/544 C
[58] Field of Search ..................................... 260/544 C

[56] References Cited

U.S. PATENT DOCUMENTS 3,639,471  2/1972  Klauke et al. ................... 260/544 C
3,998,963  12/1976  Durden, Jr. et al. ................ 424/327

Primary Examiner—Natalie Trousof
Assistant Examiner—L. Hendriksen
Attorney, Agent, or Firm—Clement J. Vicari; William Raymond Moran

[57] ABSTRACT

N-[4-(tert-butyl)phenylsulfenyl]-N-alkylcarbamoyl fluoride compounds are useful as intermediates in the preparation of pesticidally active carbamoyloxime compounds.

3 Claims, No Drawings

N-[4-(TERT-BUTYL)PHENYLSULFENYL]-N-ALKYLCARBAMOYL FLUORIDE COMPOUNDS

This application is a continuation of our prior U.S. application Ser. No. 710,738, filed Aug. 2, 1976, now abandoned.

This invention relates to novel N-[4-(tert-butyl)-phenylsulfenyl]-N-alkylcarbamoyl fluoride compounds and to their preparation. This invention also relates to a novel method of preparing 4-(tert-butyl)benzenethiol which is useful as an intermediate in the preparation of the carbamoyl fluoride compounds of this invention.

More particularly, this invention relates to compounds of the formula:

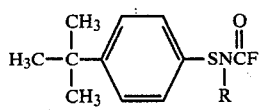

wherein R is alkyl having from 1 to 8 carbon atoms.

Illustrative of suitable R groups are alkyl groups such as methyl, ethyl, propyl, isopropyl, butyl, isobutyl, t-butyl, pentyl, hexyl, heptyl, octyl or t-octyl.

The carbamoyl fluoride compounds of this invention are useful as intermediates in the preparation of nematocidally, insecticidally, and miticidally active carbamoyloxime compounds that exhibit low levels of mammalian toxicity and phytotoxicity. One preferred compound is N-methyl-N-4-[tert-butyl)phenylsulfenyl]-carbamoyl fluoride due to its exceptional utility as an intermediate in the preparation of carbamoyloxime compounds that exhibit extremely low mammalian toxicities, exceptionally high levels of insecticidal activity against such major economic pest as aphid, armyworm and bean beetle, and low phytotoxicities against important economic crops.

The carbamoyl fluoride compounds of this invention can be reacted with either an oxime compound or a hydroxylated aromatic compound in an inert solvent in the presence of an acid acceptor to produce the corresponding pesticidally active carbamoyloxime compound. Any conventional inert solvent such as benzene, toluene, methylene chloride, tetrahydrofuran, ethyl ether, xylene or the like can be utilized in this reaction. Inorganic bases such as sodium hyrdoxide and potassium hydroxide and organic bases such as triethylamine pyridine are illustrative of bases that can be utilized as acid acceptors in the conduct of this reaction.

Illustrative of suitable oxime compounds are S-isopropylacetothiolhydroximate, S-methylacetothiolhydroximate, 2-oximino-1,4-dithiane, 5-methyl-4-oximino-1,3-oxathiolane, 5,5-dimethyl-4-oximino-1,3-dithiolane, 2-oximino-3-methyl-1,4-oxathiane, 2-methyl-2-methylthiopropionaldoxime, 1-dimethylaminocarbonyl-1-methylthioformaldoxime, 2-nitro-2-methylpropionaldoxime, 5-(2-cyanoethyl)acetothiolhydroximate, 2-oximino-1,4-dioxane, 2-oximino-1,3,5-trithiane, 2-oximino-1,3-thiazolidin-4-one, 3-oximinothiophane or the like.

Useful hydroxylated aromatic compounds are exemplified by 3-isopropylphenol, 4-methylthio-3,5-dimethylphenol, 1-naphthol, 7-hydroxy-2,2-dimethyl-2,3-dihydrobenzofuran, 3-methyl-4-dimethylaminophenol, 6-chloro-3,4-dimethylphenol, 2-isopropoxyphenol, 2-(1,3-dithiolan-2-yl)phenol, 3-methyl-4-dimethylaminomethyleneiminophenol, 4-hydroxybenzo-thiene, 4-hydroxyindane, 4-hydroxy-1,3-benzodioxalane or the like.

The carbamoyl fluoride compounds of this invention can be prepared according to a variety of methods. One preferred method of preparing the compounds of this invention is illustrated by the reaction scheme set forth below in which R is as described above.

Method I

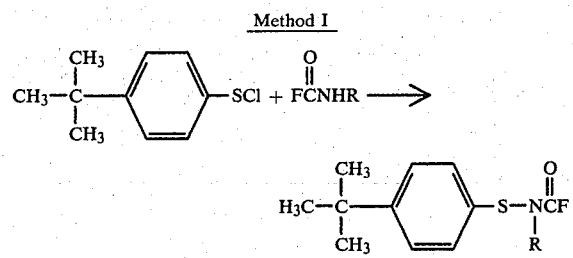

This reaction is usually carried out by contacting the reactants in an inert solvent in the presence of an acid acceptor. Illustrative of inert solvents which are useful in the conduct of this reaction are benzene, carbontetrachloride, benzene, toluene, xylene, dioxane, tetrahydrofuran, ethyl ether, cyclohexane, methylene chloride or the like.

The acid acceptor employed in this reaction is a basic material that can be either an organic or an inorganic base. The mole ratio of the acid acceptor to either 4-(t-butyl)phenylsulfenylchloride or the alkylcarbamoyl fluoride compound is substantially equimolar or, a slight excess of the acid acceptor may be used if desired. Illustrative of organic bases which may be employed as acid acceptors in the conduct of this reaction are tertiary amines, alkali metal alkoxides, alkali metal alkylides or the like. Alkali metal hydroxides, alkaline earth metal hydroxides or the like are illustrative of inorganic bases which are useful as acid acceptors. Preferred acid acceptors are tertiary amines, such as triethylamine, pryridine, 1,4-diazabicyclo[2.2.2]octane or the like.

The reaction can be conducted in either a homogeneous (monophase) system or a heterogenous (multiphase) system. In the latter case, a phase transfer agent, such as a crown ether compound, a quaternary ammonium halide compound or the like can be used to facilitate the transfer of the reactants across the phase interface.

Reaction temperatures are not critical and may be varied over a wide temperature range depending to a large extent on the reactivity and the thermal stability of the reactants. The reaction may be conducted at a temperature of from about −60° to about 100° C. The preferred reaction temperature range is from about −40° C. to about 40° C.

Reaction pressures are not critical, for convenience the reaction is usually conducted at atmospheric or autogeneous pressure. N-Alkylcarbamoyl fluoride compounds utilized as precursors in the preparation of the compounds of this invention can be conveniently prepared according to conventional methods. For example, N-alkylcarbamoyl fluoride compounds can be prepared by treating an appropriately substituted isocyanate with hydrogen fluoride. This method is described in more detail in U.S. Pat. No. 3,639,471.

The 4-tert-butylphenylsulfenyl chloride precursor can be conveniently prepared by treating 4-tert-Butylthiophenol with chlorine. 4-tert-Butylthiophenol may, in turn, be prepared according to a variety of methods.

Two novel and preferred methods are illustrated in the reaction schemes set below.

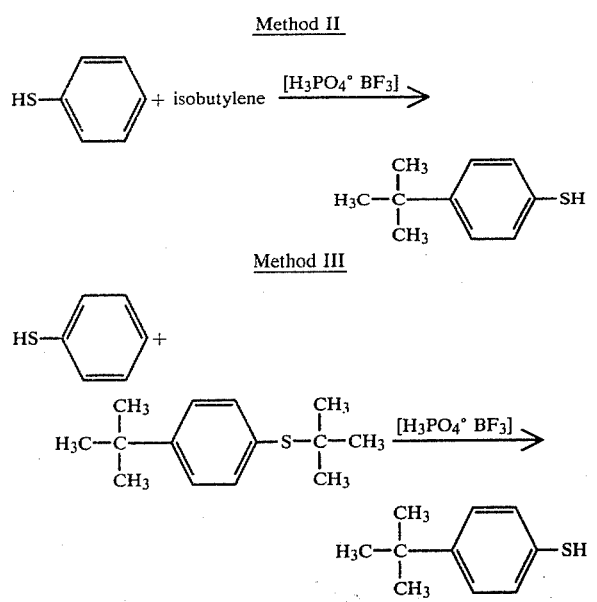

The aromatic alkylation reactions illustrated in Methods I and II are superior to other boron-trifluoride catalyzed alkylation reactions disclosed in the prior art, in that, the prior art reactions must be performed in a closed vessel, or alternatively, with the frequent addition of quantities of the catalyst throughout the course of the reaction.

The reactions illustrated in Methods II and III are conducted under similar reaction conditions. Preferably equimolar amounts of the reactants and an equivalent amount of the borontrifluoride-phosphoric acid complex($H_3PO_4 \cdot BF_3$)) catalyst are brought together either with or without a solvent. Illustrative of solvents that are useful in the conduct of this reaction are inert solvents such as benzene, toluene, xylene, dioxane, tetrahydrofuran, ethyl ether, methylene chloride or the like. These reactions are preferably conducted without a solvent.

Reaction pressures are not critical. For convenience these reactions are usually conducted at atmospheric or autogeneous pressure.

The reactions illustrated in Methods II and III can be effected at a temperature ranging from about 0° to about 130° C. and are preferably carried out at a temperature of from about 20° to about 90° C. In a preferred embodiment of the reaction of Method II, the initial reaction between thiophenol and isobutylene is carried out at a temperature of from about 0° to about 10° C. for a period of from about 0.5 to about 8 hours, after which, the reaction temperature is raised to a temperature of from about 50° to about 130° C., where it is maintained for a period of from about 0.5 to about 8 hours.

Boron trifluoride-phosphoric acid complex ($H_3PO_4.BF_3$) utilized as the catalyst in the reactions illustrated in Methods II and III can be conveniently prepared as disclosed in Friedman, H. M. and Nelson, A. L., *J. Org. Chem.*, 25 232 (1960) and references cited therein. Isobutylene and Thiophenol are well known compounds that can be either obtained from commercial source or prepared by methods known to those skilled in the art.

The following specific examples are presented to particularly illustrate the manner in which the compounds of this invention can be prepared.

EXAMPLE I

Preparation of Boron Trifluoride—Phosphoric Acid Complex

Boron trifluoride-phosphoric acid complex was prepared by the method of Friedman and Nelson (1969). In a 1000-ml four-neck flask, equipped with a thermometer, a gas diffuser, a condenser and a drying tube, 300 g (2.60 mole) of 85% phosphoric acid was saturated with boron trifluoride, with cooling and stirring to yield 585 g of borontrifluoride-phosphoric acid complex, the product which corresponded to an equimolar mixture was used as such.

EXAMPLE II

Preparation of tert-Butyl Phenyl Sulfide

To a mixture of 55 grams (0.5 mole) of thiophenol and 51 grams of boron trifluoride-phosphoric acid complex was slowly added, with stirring and cooling, 34 grams (0.6 mole) of isobutylene at 0° C. After addition was complete the mixture was stirred at 0° C. for two hours. The organic layer was separated from the catalyst layer and added to 200 ml of toluene. The toluene layer was distilled in a one-foot packed column to give 78 grams of tert-Butyl Phenyl Sulfide, b.p. 55°/3.0 mm (yield 94%). The nmr spectrum agreed with the proposed structure.

EXAMPLE III

Preparation of 4-(tert-Butyl)thiophenol

To a mixture of 1100 grams (10.0 moles) of thiophenol, and 300 grams of boron trifluoride-phosphoric acid complex was slowly added, with stirring, 620 grams (10.9 moles) of isobutylene at 0° C. After addition was complete the mixture was stirred at 0°-10° C. for two hours. The mixture was then heated to 70° C. and stirred at 70°-75° C. for two hours. The reaction mixture was cooled to 25° C. and the organic layer was separated from the lower catalyst layer and added to 500 ml of toluene. The toluene layer was washed four times with 1000-ml portions of water and then dried with magnesium sulfate. The toluene was evaporated from the mixture in vacuo and the residue was distilled in a 10-tray column to give 1120 grams of 4-(tert-butyl)-thiophenol, b.p. 58°-60°/1.00 mm (yield 68%). The nmr spectrum agreed with the structure. The residue from the above distillation was 470 grams of tert-butyl 4-(tert-butyl)phenyl sulfide. Neuworth et al (1963) report b.p. 120°/20 mm for 4-(tert-butyl)thiophenol.

EXAMPLE IV

Preparation of 4-(tert-Butyl)thiophenol

A mixture of 1285 grams (5.8 moles) of tert-butyl 4-(tert-butyl)phenyl sulfide (from replicates of EXAMPLE III) 1040 grams (9.5 moles) of thiophenol, and 350 grams of boron trifluoride-phosphoric acid complex was heated slowly to 90° C. The reaction mixture was stirred at 90° C. for four hours, cooled to 25° C., the organic layer was separated from the lower catalyst layer and added to 500 ml of toluene. This toluene solution was washed five times with 1000-ml portions of water, dried with magnesium sulfate, and then concentrated in vacuo. The residue was distilled through a 10-tray column to give 1250 grams (65% yield) of p-(tert-butyl)thiophenol, b.p. 58°–60°/1.0 mm. The nmr spectrum supported the proposed structure. A residue of 285 grams of 4-(tert-butyl)phenyl tert-butyl sulfide was obtained.

EXAMPLE V

Preparation of 4-(tert-Butyl)phenylsulfenyl Chloride

To a mixture of 332 grams (2.0 moles) of 4-(tert-butyl)thiophenol and 800 ml of carbon tetrachloride was slowly added with stirring and cooling a solution of 150 grams (2.0+ moles) of chlorine in 600 ml of carbon tetrachloride at 0° C. After chlorine addition was complete the mixture was stirred at 0°–10° C. for two hours, hydrogen chloride and carbon tetrachloride removed in vacuo and the residue was distilled in a one-foot packed column to give 378 grams of 4-(tert-butyl)phenylsulfenyl chloride, b.p. 95°–97°/1.0 mm (yield 94%).

EXAMPLE VI

Preparation of N-Methyl-N-[4-(tert-butyl)phenylsulfenyl]carbamoyl fluoride

To 1200 ml of toluene at (−40°)–(20° C.) in a one-gallon polypropylene bottle containing a stirrer, was added with stirring 37.4 grams (1.87 moles) of liquid hydrogen fluoride. The reaction mixture was raised to −10° C. and 107 grams (1.87 moles) of methyl isocyanate was added with stirring and cooling. The reaction mixture was stirred for one hour at 0° C. after the methyl isocyanate addition. To this mixture was then added 375 grams (1.87 moles) of 4-(tert-butyl)phenylsulfenyl chloride at 0° C. over a two minute period. After the 4-(tert-butyl)phenylsulfenyl chloride addition, 189 grams (1.87 moles) of triethylamine was added slowly, with cooling and stirring. The reaction mixture was then warmed to 25° C. and stirred overnight when it was added to 1000 ml of water. The toluene layer was washed four times with water and dried with magnesium sulfate after which it was distilled through a one-foot packed column to give 275 grams of N-methyl-N-[4-(tert-butyl)-phenylthio]carbamoyl fluoride, b.p. 122°/1.0 mm (yield 61%). The nmr spectrum agreed with the proposed structure.

EXAMPLE VII

Preparation of 1-(Isopropylthio)acetaldehyde O-[N-Methyl-N-[4-tert-butyl)phenylsulfenyl)carbamoyl]oxime To 2000 ml of benzene, 399 grams (3.0 moles) of 1-(isopropylthio)acetaldoxime and 726 grams (3.0 moles) of N-methyl-N-[4-(tert-butyl)phenylthio]carbamoyl fluoride in a 5000-ml round-bottom flask containing a stirrer was added slowly at 25°–35° C., 303 grams (3.0 moles) of triethylamine, with stirring and cooling. The reaction mixture was stirred at 35° C. for four hours after triethylamine addition, then stirred overnight at 25° C. The reaction mixture was then washed four times with 1000-ml portions of water and the resulting benzene layer was dried with magnesium sulfate. The benzene was removed in vacuo and the solid residue, upon crystallization from n-hexane, gave 690 grams of product, m.p. 78°–80° C., (yield 65%). The nmr spectrum of this material supported the proposed structure.

Calcd. for $C_{17}H_{26}N_2O_2S_2$: C, 57.6; H, 7.4; N, 7.9 C, 57.6; H, 7.4; N, 7.9.

What is claimed is:

1. A compound of the formula

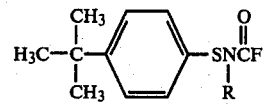

wherein R is alkyl having from 1 to 8 carbon atoms.

2. A compound according to claim 1 wherein R is alkyl having from 1 to 4 carbon atoms.

3. N-(4-tert-Butylphenylsulfenyl)-N-methylcarbamoyl fluoride.